US009572848B1

(12) United States Patent
Vascoe et al.

(10) Patent No.: US 9,572,848 B1
(45) Date of Patent: Feb. 21, 2017

(54) COMPOSITION OF MATTER FOR SEXUAL DYSFUNCTION

(71) Applicant: Aemes Research L.L.L.P., Houston, TX (US)

(72) Inventors: Jeffre Marcel Vascoe, Houston, TX (US); Ronald Edwin Merrill, Houston, TX (US)

(73) Assignee: Aemes Research L.L.L.P., Houston, TX (US)

( * ) Notice: Subject to any disclaimer, the term of this patent is extended or adjusted under 35 U.S.C. 154(b) by 0 days.

(21) Appl. No.: 14/667,770

(22) Filed: Mar. 25, 2015

Related U.S. Application Data

(60) Provisional application No. 61/970,413, filed on Mar. 26, 2014.

(51) Int. Cl.
| | | |
|---|---|---|
| *A61J 3/07* | (2006.01) | |
| *A61K 33/30* | (2006.01) | |
| *A61K 36/296* | (2006.01) | |
| *A61K 47/12* | (2006.01) | |
| *A61K 33/06* | (2006.01) | |
| *A61K 31/198* | (2006.01) | |
| *A61K 31/205* | (2006.01) | |
| *A61K 36/258* | (2006.01) | |
| *A61K 31/704* | (2006.01) | |
| *B65B 1/04* | (2006.01) | |

(52) U.S. Cl.
CPC .............. *A61K 36/296* (2013.01); *A61J 3/07* (2013.01); *A61K 31/198* (2013.01); *A61K 31/205* (2013.01); *A61K 31/704* (2013.01); *A61K 33/06* (2013.01); *A61K 33/30* (2013.01); *A61K 36/258* (2013.01); *A61K 47/12* (2013.01); *B65B 1/04* (2013.01)

(58) Field of Classification Search
CPC ........................ A61K 2300/00; A61K 36/16
USPC ................................................ 424/756, 456
See application file for complete search history.

(56) References Cited

U.S. PATENT DOCUMENTS

| | | | |
|---|---|---|---|
| 5,270,472 A | 12/1993 | Taglialatela | |
| 6,028,107 A | 2/2000 | Waugh | |
| 7,645,742 B2 | 1/2010 | Stohs | |
| 8,017,147 B2* | 9/2011 | Mazed | A61K 36/02 424/450 |
| 8,609,735 B2 | 12/2013 | Ochiai | |
| 8,802,162 B2 | 8/2014 | Greco | |
| 2004/0235953 A1 | 11/2004 | Summar | |
| 2010/0292332 A1* | 11/2010 | Ochiai | A23L 1/3051 514/565 |
| 2011/0064720 A1* | 3/2011 | Amato | A23L 1/034 424/94.65 |
| 2014/0255528 A1 | 9/2014 | Rajfer | |

OTHER PUBLICATIONS

William Davis; title: The Intimate Link between Erectile Dysfunction and Heart Disease; Life Extension Magazine; Oct. 2007, downloaded from http://www.lifeextension.com/magazine/2007/10/report_erectile_dysfunction on Jan. 4, 2016.*
Reggie Johal, title: Can Carnitine be as effective as testosterone for treating male aging symptoms?; downloaded from http://blog.predatornutrition.com/2012/04/26/.*
Sergeantnutra; title: Services: Vitamins / Minerals; downloaded from http://sergeantnutra.com/services/vitamins-and-minerals/ on Jan. 4, 2016.*
Uzunovic et al.; titel: Effect of magnesium stearate concentration on dissolution properties of ranitidine hydrochloride coated tablets;Bosnian journal of basic medical sciences; vol. 7 (3), pp. 279-283, 2007.*
Wiegel M, et al., The female sexual function index (FSFI): cross-validation and development of clinical cutoff scores, J Sex Marital Ther. 31(1):1-20 (2005).
Rosen R.C., et al., The international index of erectile function (IIEF): a multidimensional scale for assessment of erectile dysfunction. Urology 49(6):822-30 (1997).

* cited by examiner

*Primary Examiner* — Yanzhi Zhang
(74) *Attorney, Agent, or Firm* — Boulware & Valoir

(57) ABSTRACT

A composition of matter for treating sexual dysfunction is described, along with methods of making same, and methods of using same.

15 Claims, 9 Drawing Sheets

FIGURE 6
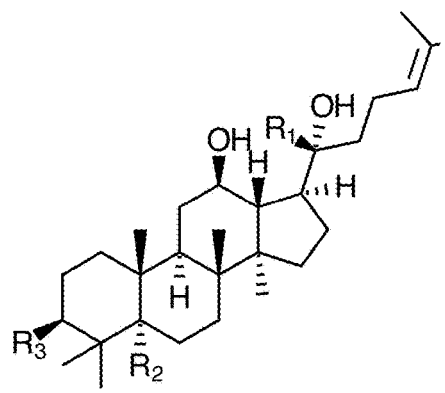
| Ginenoside | R₃ | R₂ | R₁ |
|---|---|---|---|
| Rb1 group | -O-Glc$_{(2-1)}$Glc | -H | -O-Glc$_{(6-1)}$Glc |
| Rb1 group | -OH | -O-Glc | -O-Glc |
| Glc: Glucopyranoside (β-D-Glucose) <br> Subscripts indicate the carbon in the glucose rings linking the two carbohydrates ||||
FIGURE 7: DHEA
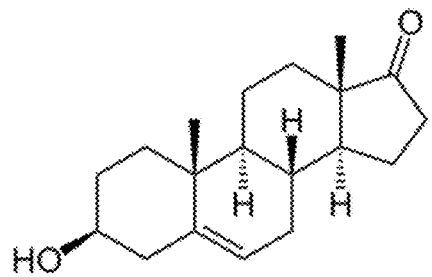

FSFI Full Scale

○ Group 1: FSFI Full Scale baseline mean = 12.967
◇ Group 2: FSFI Full Scale baseline mean = 23.740

FSFI Desire

○ Group 1: FSFI Full Scale baseline mean = 12.967
◇ Group 2: FSFI Full Scale baseline mean = 23.740

FIGURE 17A

| Ingredient | Daily mg (elemental) | | | | | |
|---|---|---|---|---|---|---|
| | Stronvivo | Stronvivo Plus | Stronvivo Max | Stronvivo Anti-Oxidant | Stronvivo Anti-Oxidant Plus | Stronvivo Anti-Oxidant Max |
| L-Arginine | 2000 | 2000 | 6000 | 2000 | 2000 | 6000 |
| L-Citrulline | 1000 | 1000 | 4000 | 1000 | 1000 | 4000 |
| L-Carnitine | 1000 | 1000 | 2000 | 1000 | 1000 | 2000 |
| Magnesium | 64 | 400 | 400 | 64 | 400 | 400 |
| Zinc | 10.5 | 30 | 30 | 10.5 | 30 | 30 |
| Vitamin C | | | | 2000 | 2000 | 2000 |
| Vitamin A | | | | 0.8 | 0.8 | 0.8 |
| Vitamin E | | | | 400 | 400 | 400 |
| Vitamin D3 | | | | | | |
| Vitamin B12 | | | | | | |
| Folic Acid (B9) | | | | | | |
| CoQ10 | | | | | | |
| D-Ribose | | | | | | |
| Alpha LIpoic Acid (ALA) | | | | | | |
| L-taurine | | | | | | |

FIGURE 17 B

| Ingredient | Daily mg (elemental) | | | | | |
|---|---|---|---|---|---|---|
| | Stronvivo Boost | Stronvivo Boost Plus | Stronvivo Boost Max | Stronvivo Endothelium | Stronvivo Endothelium Plus | Stronvivo Endothelium Max |
| L-Arginine | 2000 | 2000 | 6000 | 2000 | 2000 | 6000 |
| L-Citrulline | 1000 | 1000 | 4000 | 1000 | 1000 | 4000 |
| L-Carnitine | 1000 | 1000 | 2000 | 1000 | 1000 | 2000 |
| Magnesium | 64 | 400 | 400 | 64 | 400 | 400 |
| Zinc | 10.5 | 30 | 30 | 10.5 | 30 | 30 |
| Vitamin C | | | | | 500 | 2000 |
| Vitamin A | | | | | | |
| Vitamin E | | | | | 200 | 200 |
| Vitamin D3 | 0.25 | 0.4 | 0.4 | | | |
| Vitamin B12 | 1 | 1.5 | 1.5 | | | |
| Folic Acid (B9) | 0.5 | 1 | 1 | 0.5 | 1 | 1 |
| CoQ10 | | | | 200 | 300 | 400 |
| D-Ribose | | | | 4000 | 4500 | 5000 |
| Alpha LIpoic Acid (ALA) | | | | | 300 | 600 |
| L-taurine | | | | | | 2000 |

COMPOSITION OF MATTER FOR SEXUAL DYSFUNCTION

PRIOR RELATED APPLICATIONS

This application claims priority to U.S. Ser. No. 61/970,413, filed Mar. 26, 2014, which is incorporated by reference herein in its entirety for all purposes.

FEDERALLY SPONSORED RESEARCH STATEMENT

Not applicable.

FIELD OF THE DISCLOSURE

The disclosure generally relates to compositions of matter that can beneficially used in the treatment of sexual dysfunction, or as nutritional support for same, as well as for other conditions. Methods of making and using these compositions are also provided.

BACKGROUND OF THE DISCLOSURE

Arginine is a conditionally nonessential amino acid, meaning that most of the time it can be manufactured by the human body, and does not need to be obtained directly through the diet. The biosynthetic pathway, however, does not produce sufficient arginine, and some must still be consumed. Individuals with poor nutrition or certain physical conditions may need to increase their intake of foods containing arginine or take arginine supplements.

Arginine is synthesized from citrulline by the sequential action of the cytosolic enzymes argininosuccinate synthetase (ASS) and argininosuccinate lyase (ASL). In terms of energy, this is costly, as the synthesis of each molecule of argininosuccinate requires hydrolysis of adenosine triphosphate (ATP) to adenosine monophosphate (AMP), i.e., two ATP equivalents. In essence, taking an excess of arginine gives more energy by saving ATPs that can be used elsewhere.

Citrulline can be derived from multiple sources:
from arginine via nitric oxide synthase (NOS)
from ornithine via catabolism of proline or glutamine/glutamate
from asymmetric dimethylarginine (ADMA) via DDAH On a whole-body basis, synthesis of arginine occurs principally via the intestinal-renal axis, wherein epithelial cells of the small intestine, which produce citrulline primarily from glutamine and glutamate, collaborate with the proximal tubule cells of the kidney, which extract citrulline from the circulation and convert it to arginine, which is returned to the circulation. As a consequence, impairment of small bowel or renal function can reduce endogenous arginine synthesis, thereby increasing the dietary requirement.

Synthesis of arginine from citrulline also occurs at a low level in many other cells, and cellular capacity for arginine synthesis can be markedly increased under circumstances that also induce iNOS. Thus, citrulline, a co-product of the NOS-catalyzed reaction, can be recycled to arginine in a pathway known as the citrulline-NO or arginine-citrulline pathway. This is demonstrated by the fact that, in many cell types, citrulline can substitute for arginine to some degree in supporting NO synthesis. However, recycling is not quantitative because citrulline accumulates along with nitrate and nitrite, the stable end-products of NO, in NO-producing cells.

Arginine plays an important role in cell division, the healing of wounds, removing ammonia from the body, immune function, and the release of hormones.

The roles of arginine include:
Precursor for the synthesis of nitric oxide (NO). Non-L-arginine derived NO can be generated by the nitrate-nitrite-nitric oxide pathway that is monitored through saliva testing.
Reduces healing time of injuries (particularly bone).
Quickens repair time of damaged tissue.
Helps decrease blood pressure in clinical hypertensive subjects. NO-mediated decrease in blood pressure is influenced by both the L-arginine-dependent nitric oxide synthase pathway and non-L-arginine or alternative pathway through nitrate-rich foods such as beets and spinach.

Arginine is the immediate precursor of nitric oxide (NO), urea, ornithine, and agmatine; is necessary for the synthesis of creatine; and can also be used for the synthesis of polyamines (mainly through ornithine and to a lesser degree through agmatine), citrulline, and glutamate. As a precursor of nitric oxide, arginine may have a role in the treatment of some conditions where vasodilation is required. The presence of asymmetric dimethylarginine (ADMA), a close relative, inhibits the nitric oxide reaction; therefore, ADMA is considered a marker for vascular disease, just as L-arginine is considered a sign of a healthy endothelium.

Intravenously-administered arginine stimulates the secretion of growth hormone, and is used in growth hormone stimulation tests. Two studies have found that oral arginine supplementation is also effective at increasing resting GH levels. The first study found that oral preparations of arginine are effective at increasing growth hormone levels. In fact, the 9-gram dose resulted in mean peak GH levels of 6.4 (+/−1.3) μg/L versus placebo levels of 2.9 (+/−0.7). Another study found similar results. It included resting versus exercise and oral L-arginine versus oral placebo. The authors concluded that "Oral arginine alone (7 g) stimulated GH release, but a greater GH response was seen with exercise alone. The combined effect of arginine before exercise attenuates the GH response . . . GH production: Ex>Arg+Ex>Arg>placebo" suggesting against supplementing with arginine alone prior to exercise if the goal is to raise GH levels, but concurring with the previous study that oral L-arginine increases GH on days free of significant exercise.

In contrast to these two studies that found increased resting GH due to oral arginine supplementation, a third study did not find increase in resting GH levels from oral supplementation. In that study, oral preparations of L-arginine were ineffective at increasing growth hormone levels despite being effective at increasing plasma levels of L-arginine. However, bioavailability data was not available, and it is possible that quality, stability and/or uptake was a problem.

Intravenous infusion of arginine reduces blood pressure in patients with hypertension as well as normal subjects. A meta-analysis showed that L-arginine reduces blood pressure with pooled estimates of 5.4/2.7 mmHg for SBP/DBP. Supplementation with L-arginine reduces diastolic blood pressure and lengthens pregnancy for women with gestational hypertension, including women with high blood pressure as part of pre-eclampsia. It does not, however, lower systolic blood pressure or improve the baby's weight at birth.

Carnitine is another important biological molecule. It is a quaternary ammonium compound biosynthesized from the amino acids lysine and methionine. Carnitine exists in two stereoisomers: its biologically active form is L-carnitine, whereas its enantiomer, D-carnitine, is biologically inactive.

In eukaryotic cells, carnitine is required for the transport of fatty acids from the intermembraneous space in the mitochondria, into the mitochondrial matrix during the breakdown of lipids (fats) for the generation of metabolic energy, and is widely available as a nutritional supplement. Carnitine was originally found as a growth factor for mealworms and labeled vitamin BT, although carnitine is not a proper vitamin.

Carnitine transports long-chain acyl groups from fatty acids into the mitochondrial matrix, so they can be broken down through β-oxidation to acetyl CoA to obtain usable energy via the citric acid cycle. Fatty acids must be activated before binding to the carnitine molecule to form 'acylcarnitine'. The free fatty acid in the cytosol is attached with a thioester bond to coenzyme A (CoA). This reaction is catalyzed by the enzyme fatty acyl-CoA synthetase and driven to completion by inorganic pyrophosphatase.

The acyl group on CoA can now be transferred to carnitine and the resulting acylcarnitine transported into the mitochondrial matrix. This occurs via a series of similar steps:
  Acyl CoA is transferred to the hydroxyl group of carnitine by carnitine acyltransferase I (palmitoyltransferase) located on the outer mitochondrial membrane.
  Acylcarnitine is shuttled inside by a carnitine-acylcarnitine translocase.
  Acylcarnitine is converted to acyl CoA by carnitine acyltransferase II (palmitoyltransferase) located on the inner mitochondrial membrane. The liberated carnitine returns to the cytosol.

Human genetic disorders, such as primary carnitine deficiency, carnitine palmitoyltransferase I deficiency, carnitine palmitoyltransferase II deficiency and carnitine-acylcarnitine translocase deficiency, affect different steps of this process.

Carnitine acyltransferase I and peroxisomal carnitine octanoyl transferase (CROT) undergo allosteric inhibition as a result of malonyl-CoA, an intermediate in fatty acid biosynthesis, to prevent futile cycling between β-oxidation and fatty acid synthesis.

There may be a link between dietary consumption of carnitine and atherosclerosis, but there is also evidence that it lowers the risk of mortality and arrythmias after an acute myocardial infarction.

When certain species of intestinal bacteria were exposed to carnitine from food, they produced a waste product, trimethylamine, which is transformed in the liver to trimethylamine N-oxide (TMAO). TMAO may be associated with atherosclerosis. The presence of large amounts of TMAO-producing bacteria was a consequence of a long-term diet rich in meat. However, when the authors compared the risk of cardiovascular events to the levels of carnitine and TMAO, they found that the risk was higher in those with higher TMAO levels, independent of the carnitine levels.

Vegetarian and vegans who ate a single meal of meat had much lower levels of TMAO in their bloodstream than did regular meat-eaters, as vegetarian and vegans had lower levels of the intestinal bacteria that converts carnitine into TMAO.

Another study has found evidence of a second path for atherogenic activity of carnitine, passing through a different metabolite: γ-butyrobetaine (γBB)

In the course of human aging, carnitine concentration in cells diminishes, affecting fatty acid metabolism in various tissues. Particularly adversely affected are bones, which require continuous reconstructive and metabolic functions of osteoblasts for maintenance of bone mass. A 2008 study found that supplementing with L-carnitine decreased bone turnover and increased bone mineral density in rats.

A 2004 study found that L-carnitine acts as a peripheral antagonist of thyroid hormone action. In particular, L-carnitine inhibits both triiodothyronine (T3) and thyroxine (T4) entry into the cell nuclei. For this reason, L-carnitine has been proposed as a supplement to treat hyperthyroidism. A 2001 study found that L-carnitine was useful in both reversing and preventing hyperthyroid symptoms.

Carnitine has been proposed as a supplement to treat a variety of health conditions including heart attack, heart failure, angina, narcolepsy, and diabetic neuropathy, but not fatigue, improving exercise performance, nor wasting syndrome (weight loss). There is also some suggestion that use of acetyl-carnitine and L-arginine may improve sperm motility in men with sperm abnormalities.

Dehydroepiandrosterone/dehydroepiandrostenedione (DHEA, more correctly didehydroepiandrosterone), also known as androstenolone or prasterone (INN), as well as 3β-hydroxyandrost-5-en-17-one or 5-androsten-3β-ol-17-one, is an important endogenous steroid hormone. It is the most abundant circulating steroid hormone in humans, in whom it is produced in the adrenal glands, the gonads, and the brain, where it functions predominantly as a metabolic intermediate in the biosynthesis of the androgen and estrogen sex steroids. However, DHEA also has a variety of potential biological effects in its own right, binding to an array of nuclear and cell surface receptors, and acting as a neurosteroid.

Zinc and magnesium are also essential elements in the human body. Zinc is an essential trace element for humans, is found in hundreds of enzymes, serves as structural ions in transcription factors and is stored and transferred in metallothioneins. It is typically the second most abundant transition metal in organisms after iron and it is the only metal which appears in all enzyme classes.

There are 2-4 grams of zinc distributed throughout the human body. Most zinc is in the brain, muscle, bones, kidney, and liver, with the highest concentrations in the prostate and parts of the eye. Semen is particularly rich in zinc, which is a key factor in prostate gland function and reproductive organ growth.

In humans, zinc interacts with a wide range of organic ligands, and has roles in the metabolism of RNA and DNA, signal transduction, and gene expression. It also regulates apoptosis. A 2006 study estimated that about 10% of human proteins (2800) potentially bind zinc, in addition to hundreds which transport and traffic zinc; a similar in silico study in the plant *Arabidopsis thaliana* found 2367 zinc-related proteins.

In the brain, zinc is stored in specific synaptic vesicles by glutamatergic neurons and can modulate brain excitability. It plays a key role in synaptic plasticity and so in learning. However, it has been called "the brain's dark horse" because it also can be a neurotoxin, suggesting zinc homeostasis plays a critical role in normal functioning of the brain and central nervous system.

Because of the important interaction between phosphate and magnesium ions, magnesium ions are essential to the basic nucleic acid chemistry of life, and thus are essential to all cells of all known living organisms. Over 300 enzymes require the presence of magnesium ions for their catalytic action, including all enzymes utilizing or synthesizing ATP, or those that use other nucleotides to synthesize DNA and RNA. ATP exists in cells normally as a chelate of ATP and a magnesium ion.

Magnesium deficiency (hypomagnesemia) is common and vastly under reported: it is found in 2.5-15% of the general population but may be much higher due to the body's attempt to keep blood magnesium levels relatively stable by releasing magnesium from bone and tissues. So, even though the blood level may be normal, the body may actually be deficient. The primary cause of deficiency is decreased dietary intake: only 32% of people in the United States meet the recommended daily allowance. Other causes are increased renal or gastrointestinal loss, an increased intracellular shift, and proton-pump inhibitor antacid therapy. Most are asymptomatic, but symptoms referable to neuromuscular, cardiovascular, and metabolic dysfunction may occur. Alcoholism is often associated with magnesium deficiency. Chronically low serum magnesium levels are associated with metabolic syndrome, diabetes mellitus type 2 and hypertension.

Not surprisingly, the patent literature is replete with medical uses for these molecules and trace elements, or uses as nutritional support uses for certain disease states. However, there is always room for improved formulations designed to treat specific conditions.

SUMMARY OF THE DISCLOSURE

The invention generally relates to pharmaceutical grade compositions of matter that can be used to treat sexual dysfunction, as well as to methods of making and using same.

Formulae 1 was actually tested in men and women with sexual dysfunction, each taking the formulae for 90 days. The study sample included 59 adults (m/f 51/8), ages 30-84, BMI 21-56. Patients were administered 6 capsules of Formula 1 daily for 90 days, which equated to a total daily intake of 2,000 mg of L-arginine, 1,000 mg of L-citrulline, 1,000 mg of L-carnitine, 30 mg of zinc sulfate, and 400 mg of magnesium citrate. Patients were assessed at four time points: baseline (prior to supplementation), 30-day follow-up, 60-day follow-up and 90-day follow-up. Measures included: FSFI, IIEF, PHQ-9 and ADAM.

Mean scores on the subscales of the FSFI, (i.e., Desire, Arousal, Lubrication, Orgasm, Satisfaction, Pain) demonstrated linear improvement. Mean full-scale FSFI scores were as follows: baseline M=19.70; 30-day M=23.94; 60-day M=27.79; and 90-day M=31.75 with improvements shown in the domains of Desire (2.10), Arousal (2.30), Lubrication (2.28), Orgasm (2.00), Satisfaction (1.45) and Pain (2.15). For males, significant improvement was noted in terms of IIEF total scores from baseline (M=43.65) to 60 days (M=52.40). Ratings of erectile dysfunction improved from baseline to 60 days and ratings of sexual desire and overall satisfaction improved from baseline to all other time points. On the ADAM, over half the sample meeting criteria for androgen deficiency at baseline no longer met criteria after 30 days (n=22; 51%). Finally, significant improvement in depressive symptoms (PHQ-9) was noted for males after 30 days and for females after 60 days.

Although results must be interpreted with caution, females reported improvements in all areas of sexual functioning, as well as significant improvements in subjective mood while taking Formula 1. Males reported improved erectile function, desire and satisfaction following initiation of Formula 1. Further, taking Formula 1 for a month led to reduced symptoms of androgen deficiency and significant improvements in subjective mood.

The invention includes one or more of the following embodiments, in any combination(s) thereof:

- A composition of matter, comprising 1-2 parts L-arginine, 1-2 parts L-citrulline, 1-2 parts L-carnitine, and one or more of 0-0.05 parts zinc, 0-0.6 parts magnesium, 0-1 part *ginseng*, and 0-1.2 parts *Epimedium*. Preferred compositions are disclosed throughout this specification, and especially preferred is Formula 1 because of its proven efficacy in both male and female sexual dysfunction.
- A composition as herein described, formulated as a time release formulation, preferably formulated with magnesium stearate or a coating thereof to slow dissolution.
- A composition as herein described, said carnitine as carnitine tartrate, said zinc as zinc sulfate, and said magnesium as magnesium citrate.
- A composition as herein described, wherein every ingredient is pharmaceutical grade.
- A composition as herein described, in the form of pellets inside a capsule, or in the form of time-release pellets inside a gelatin capsule.
- A method of treating sexual dysfunction, comprising administering a composition as herein described to a patient having a sexual dysfunction in an amount providing about 2 g of L-Arginine, and about 1 g each of L-citrulline and L-carnitine daily for a period of at least 30 days. Preferably, the method comprises administering the composition for a period of at least 60 days or more preferably, a period of at least 90 days.
- A method as herein described, wherein said sexual dysfunction is female sexual arousal disorder (FSAD), female orgasmic disorder (FOD), and hypoactive sexual desire disorder (HSDD), erectile dysfunction (ED), or depression.
- A method of making a composition of matter for treating sexual dysfunction, said method comprising: a) blending the active ingredients herein described, b) making pellets from the blend of step a); and c) filling capsules with the pellets of step b). Preferably, the method includes coating said pellets with magnesium stearate or otherwise making a extended release formulation.

Preferably, the L form of the molecules are used herein rather than a racemic mixture, as frequently the opposite chirality may have no effect or even toxic effect.

What is meant by a pharmacologically acceptable salt of L-carnitine, L arginine, L-carnetine and the like, is any salt of these with an acid which does not give rise to unwanted toxic or side effects. These acids are well known to pharmacologists and to experts in pharmaceutical technology.

Non-limiting examples of such salts are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

Esters of acids can also be used in place of the acids, especially acyl esters of carnitine, and the like, provided the esters are nontoxic.

As used herein "time release" technology (also known as sustained-release [SR], extended-release [ER, XR, XL], controlled-release [CR], and other synonyms or near-synonyms) is a mechanism used in pill tablets or capsules to dissolve a drug over time in order to be released slower and steadier into the bloodstream while having the advantage of being taken at less frequent intervals than immediate-release (IR) formulations of the same drug.

One preferred time release formulation is a capsule containing a multitude of small granules or beads, referred to as "spheroids" or "pellets". Each spheroid is comprised of a core, and a coating applied to the core. The core is comprised of active ingredients, sometimes mixed with a dispersing agent, buffers, stabilizers and the like, The cores can be made, e.g., by mixing ingredients with water or other solvent to produce a wet plastic mass, which is then extruded, spheronized and dried. The cores are coated with a mixture of e.g., ethylcellulose and hydroxypropylmethylcellulose. The ethylcellulose makes the film water-insoluble, while the hydroxypropylmethylcellulose makes the film water-permeable. The film coating is then applied by dissolving the ethylcellulose and hydroxypropylmethylcellulose in solvent, and spraying the solution onto the cores in a fluid bed drying system. The result is slow release by permeation through the film, with the release rate dependent on the ratio of hydroxypropylmethylcellulose to ethylcellulose and the thickness of the coat.

The above formulation provides the following time release profile.

| Time (hours) | % Released |
| --- | --- |
| 2 | <30 |
| 4 | 30-60 |
| 8 | 60-90 |
| 12 | >90 |

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, buffers, non-active excipients, food coloring, flavoring, and the like.

The following abbreviations are used herein:

| ABBREVIATION | TERM |
| --- | --- |
| AD | Androgen deficiency |
| API | Active pharmaceutical ingredient |
| CD | controlled delivery |
| CR | controlled release |
| DHEA | Dehydroepiandrosterone |
| DR | delayed release |
| ER | extended release |
| FDA | Food and Drug Administration |
| FOD | female orgasmic disorder |
| FSAD | female sexual arousal disorder |
| HSDD | hypoactive sexual desire disorder |
| IR | immediate release |

-continued

| ABBREVIATION | TERM |
| --- | --- |
| LA | long acting |
| MR | modified release |
| SA | sustained action |
| SR | sustained release |
| TR | timed release |
| WADA | World Anti-Doping Agency |
| XL | extended release |
| XR | extended release |
| XT | extended release |

BRIEF DESCRIPTION OF THE DRAWINGS

FIG. 6: Ginsenosides
FIG. 7: DHEA

DETAILED DESCRIPTION

Figure 1:
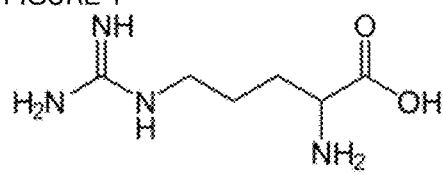
FIG. 1: ARGININE
Figure 2:
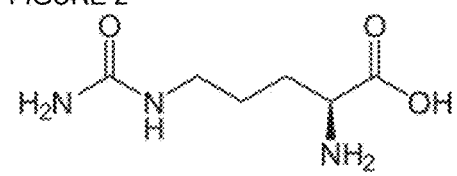
FIG. 2: CITRULLINE
Figure 3:
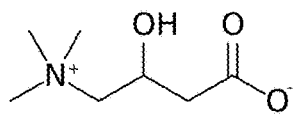
FIG. 3: CARNITINE
Figure 4:
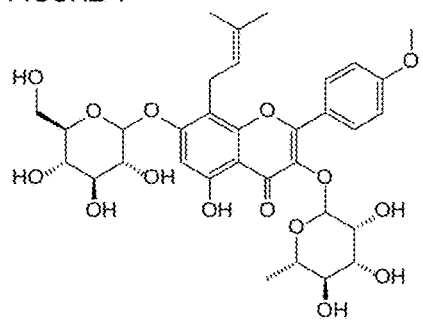
FIG. 4: ICARIIN
Figure 5:
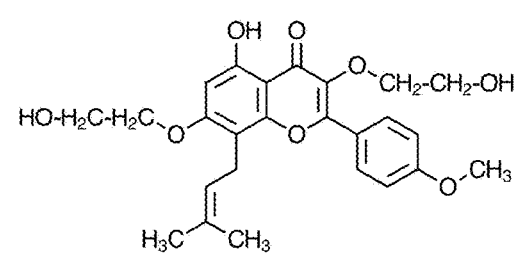
FIG. 5: 3,7-bis(2-hydroxyethyl)icaritin
Figure 8:
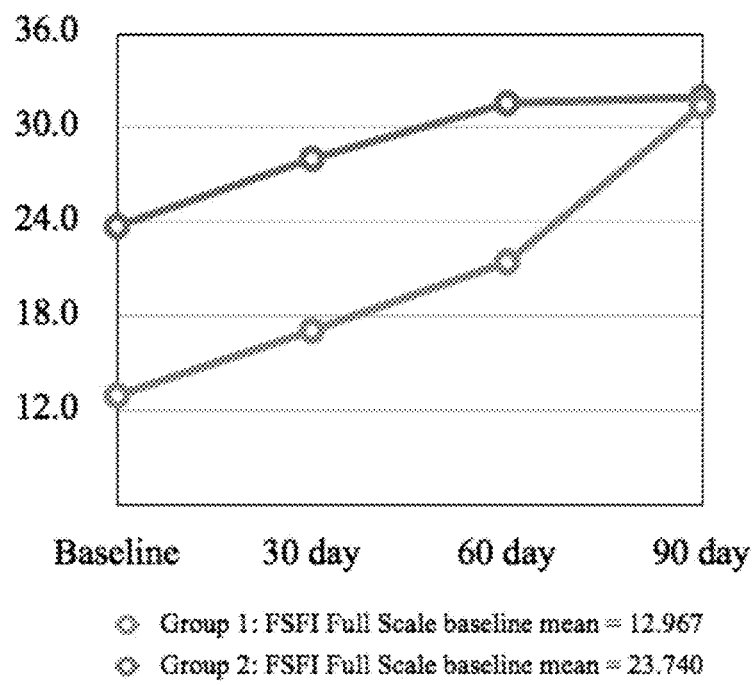
FIG. 8: FSFI FULL SCALE
Figure 9:
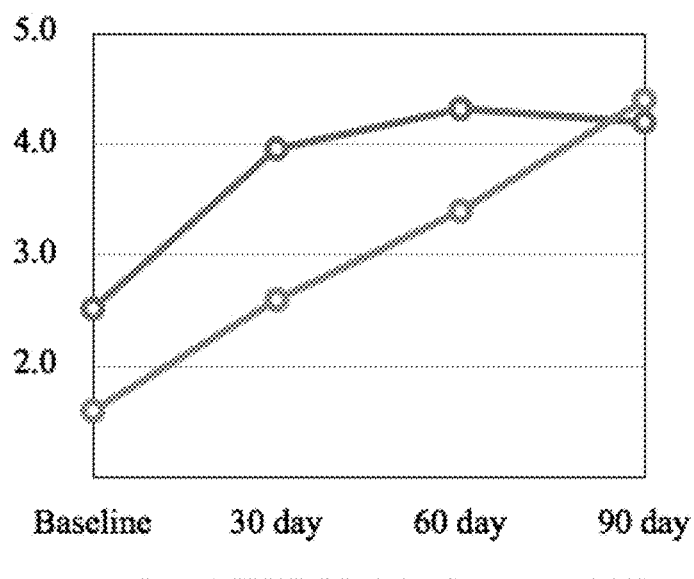
FIG. 9: FSFI DESIRE
Figure 10:
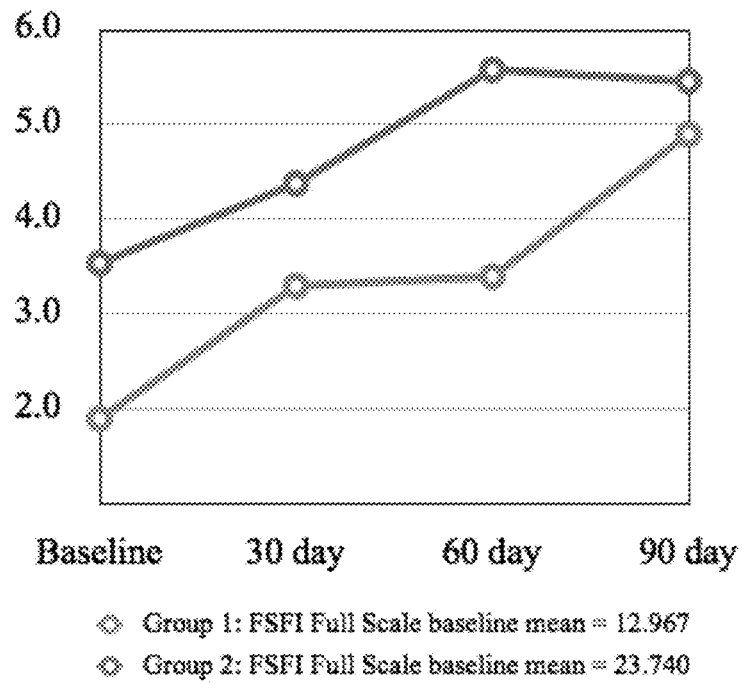
FIG. 10: FSFI AROUSAL
Figure 11:
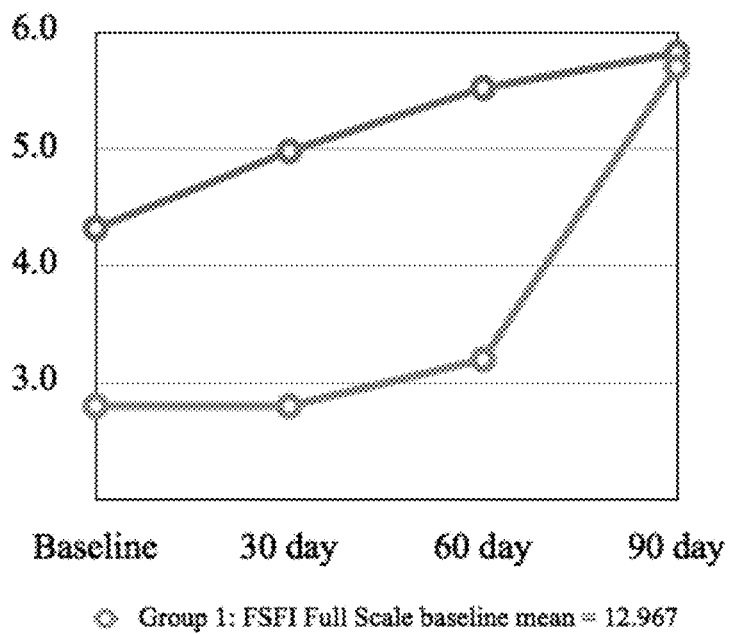
FIG. 11: FSFI LUBRICATION
Figure 12:
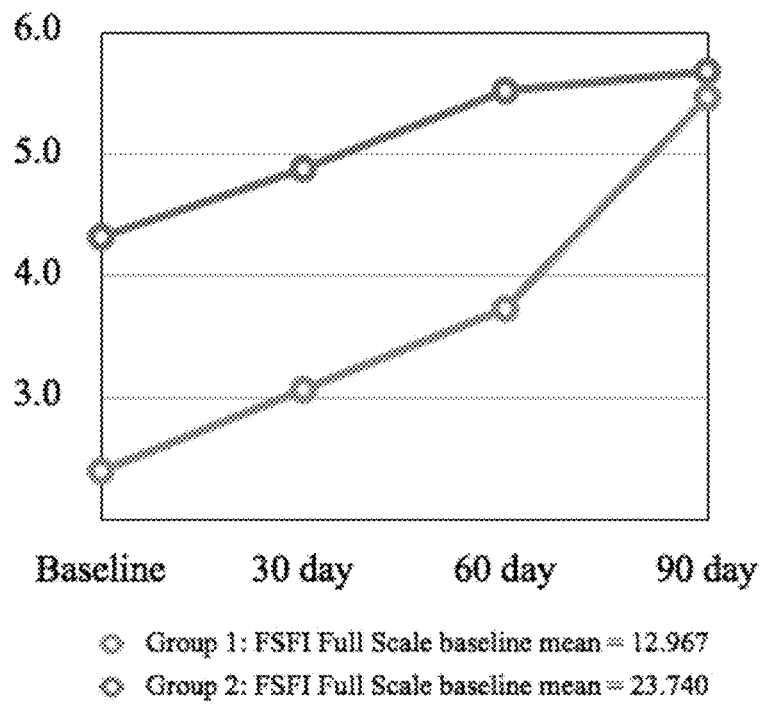
FIG. 12: FSFI ORGASM
Figure 13:
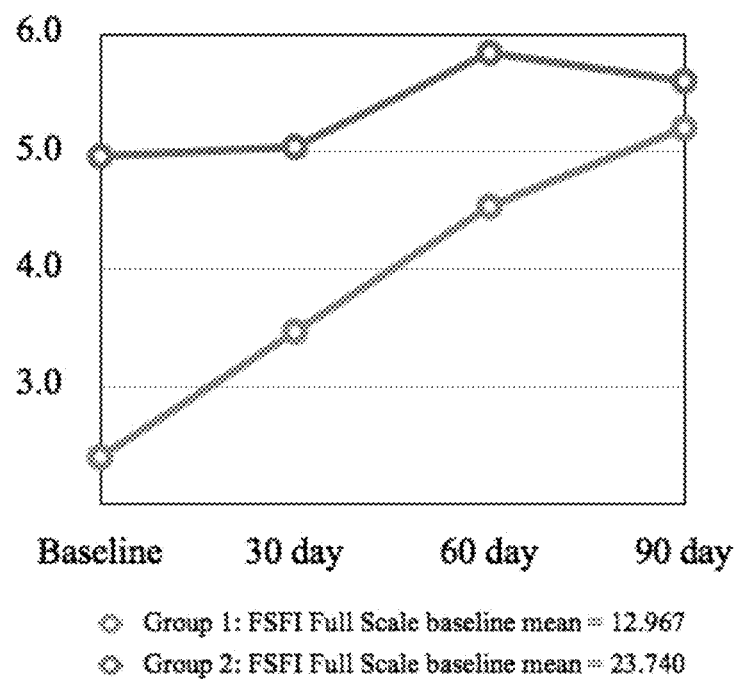
FIG. 13: FSFI SATISFACTION
Figure 14:
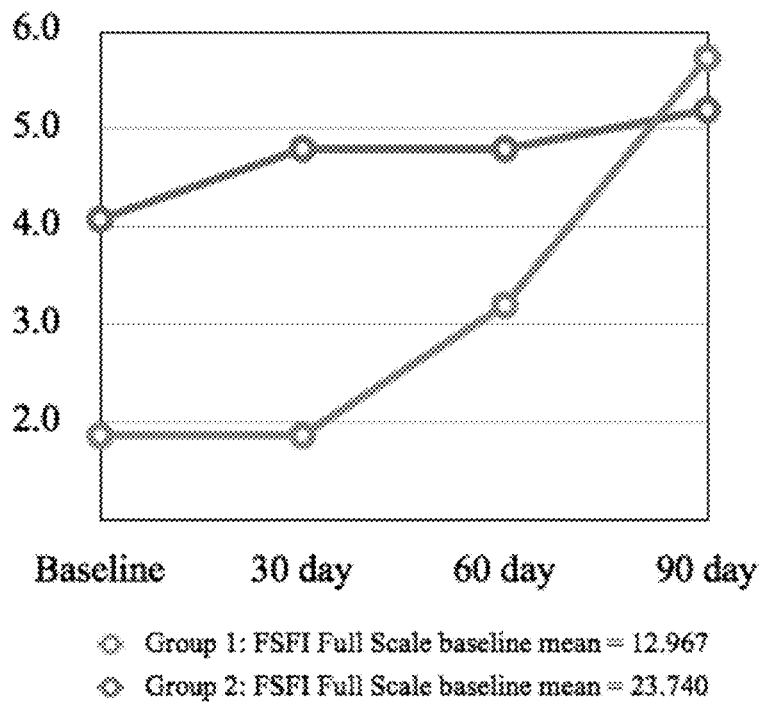
FIG. 14: FSFI PAIN

One embodiment of the invention discloses a pharmaceutical composition comprising 1-2 parts L-arginine, 1-2 parts L-citrulline, 1-2 parts L-carnitine, and one or more of 0.02-0.05 parts zinc, 0.3-0.5 parts magnesium, 0.5-1 part Korean *ginseng*, and 0.7-1.2 parts *epimedium*. Preferably, the composition is formulated as a time release formulation.

Other embodiments provide the following specific formulations:

1000-2000 mg L-Arginine, 500-1500 mg L-Citrulline, 500-1500 mg L-Carnitine, 25-50 mg Zinc, 300-500 mg Magnesium, plus 0-1500 mg Korean *Ginseng*, 0-1200 mg Horny Goat weed, 0-100 mg DHEA.

2000-4000 mg L-Arginine, 1000-2000 mg L-Citrulline, 1000-2000 mg L-Carnitine, 10-40 mg Zinc, 100-400 mg Magnesium 1-2 parts L-arginine, 1-2 parts L-citrulline, 1-2 parts L-carnitine, and one or more of 0-0.05 parts zinc, 0-0.6 parts magnesium, 0-1 part *ginseng* or 0-0.5 parts of the active ingredients thereof, and 0-1.2 parts *Epimedium* or 0-0.5 parts of icariin.

1000 mg L-Arginine, 1000 mg L-Citrulline, 1000 mg L-Carnitine, 900 mg Korean *Ginseng*, 1000 mg Horny Goat Weed, 50 mg DHEA.

2000 mg L-Arginine, 2000 mg L-Citrulline, 2000 mg L-Carnitine, 30 mg Zinc, 400 mg Magnesium, 900 mg Korean *Ginseng*.

1000 mg L-Arginine, 1000 mg L-Citrulline, 1000 mg L-Carnitine, 500 mg ginsenosides, 50-100 mg icariin, and 25-50 mg DHEA The disclosure provides a preferred composition comprising L-Arginine, L-Citrulline, L-Carnitine, Zinc, and Magnesium, preferably containing 2000 mg L-Arginine, 1000 mg L-Citrulline, 1000 mg L-Carnitine, 30 mg Zinc, 400 mg Magnesium in a daily dose thereof, and preferably formulated as an extended release formulation releasing active ingredients for at least 12 hrs.

Additional formulations are provided in FIGS. 17A-B.

L-Arginine, L-Citrulline, L-Carnitine, Zinc, Magnesium, and derivatives of same are available from many manufactures in >95% purity, >98% purity, >99% purity, as well as ultrapure, food grade and pharm grade chemicals.

The compositions herein provided can be formulated as a pill, a hard gelatin capsule, a soft gelatin capsule, a dissolving oral strip, a powder, a drink or liquid concentrate, a chewing gum, and the like. A soft gelatin capsule may be preferred as easy to manufacture as well as administer. The composition may also be formulated as part of a food product. In one embodiment, the composition is a powder that may be solubilized in a liquid for ingestion. In another embodiment, a capsule is provided with time release ingredients.

The ingredients can be blended as dried powders, or blended with a volatile liquid, which is then evaporated. The blended ingredients can be mixed with pharmaceutically acceptable excipients, such as fillers, dessicants, and the like, as appropriate for the chosen administration method.

For example, a tablet is usually a compressed preparation that contains 5-10% of the drug (active substance); about 80% of fillers, disintegrants, lubricants, glidants, and binders; and about 10% of compounds to ensure easy disintegration, disaggregation, and dissolution of the tablet in the stomach or the intestine.

As another example, the capsules contain active ingredients in an erodible matrix, comprising povidone, hydroxyethyl cellulose, microcrystalline cellulose, magnesium oxide, colloidal silicon dioxide and magnesium stearate as described in U.S. Pat. No. 6,274,168 and US20010043945. Alternatively, EudragitL-100 can be used as enteric coating polymer and the pellets coated by pan coating technique. U.S. Pat. No. 5,968,554 discloses a sustained release formulation containing drug, a first enteric coating over the core, a second coating of the active ingredient, and a third coating that is soluble in gastric juices. Other methods are described, e.g., in U.S. Pat. No. 6,274,168 and U.S. Pat. No. 6,620,432. Each of these is incorporated by reference herein in its entirety for all purposes.

An extended released formulation can be made by forming a plurality of discrete particles containing API as described herein, which, when contained within a gelatin capsule and assayed in a USP Apparatus I rotating basket at 50 rpm in 900 mL of phosphate buffer at pH 5.8 and 37° C., exhibits delays release, such that drug is continually released for about 12-24 hrs. Preferably, the blood stream levels are relatively constant with those 12-24 hrs.

Capsule delivery may be preferred as very easy to make and to administer, yet capable of providing variable release formulations. The capsules themselves can be designed to remain intact for some hours after ingestion in order to delay absorption. Alternatively, they may contain a mixture of slow- and fast-release particles to produce rapid and sustained absorption in the same dose. In a preferred embodiment, the blended powders are made into small pellets, which are then coated to provided delayed release or variable release, and this mixture is then placed into a capsule, the capsule assembled and packaged for use.

In another embodiment of the invention, the composition may further include a number of inactive ingredients, such as effervescent combinations, diluents, buffers, preservatives, desiccants, thickeners, fillers, flavorings, sweeteners, colorings and any other excipients or inactive ingredients known in the art.

In one embodiment of the invention, the composition includes an effervescent combination. The effervescent combination may include any combination of at least one acid and at least one base known in the art to produce an effervescent effect that is safe for use in food or pharmaceuticals. Examples of suitable acids may include citric acid, tartaric acid, aspartic acid or malic acid and combinations thereof. Examples of suitable bases may include sodium carbonate, potassium bicarbonate or sodium bicarbonate and combinations thereof.

The compositions are particularly useful in sexual dysfunction, such as female sexual arousal disorder (FSAD), female orgasmic disorder (FOD), and hypoactive sexual desire disorder (HSDD); erectile dysfunction (ED), androgen deficiency (AD), depression and the like However, the composition is expected to have potential in a great number of conditions, based on available literature on the various components. Thus, the composition may aid in one or more of the following:

1. Improves the health of the endothelium
2. Improves the health of endothelial cells
3. Protects a healthy endothelium
4. Protects healthy endothelial cells
5. Stops decaying endothelium from further decay
6. Stops decaying endothelial cells from further decay
7. Causes the body to create a higher volume of endothelial cells
8. Improves the formation and quality of new endothelial cells produced
9. Increases endogenous nitric oxide production
10. Increases the volume of circulating endothelia progenitor cells
11. Increases the effectiveness of circulating endothelia progenitor cells
12. Increases the bone marrow production of stem cells
13. Increases the circulating stem cells
14. Increases the concentration of stem cells at damaged organ tissue
15. Stimulates liver regeneration
16. Reverses the age-driven decrease in nitric oxide production
17. Reverses the age-driven decrease in endothelium function
18. Reverses the age-driven decrease in endothelial cell quality
19. Increases testosterone production
20. Slows the decay of testosterone
21. Causes existing testosterone to be more effective
22. Increases effectiveness of supplemental testosterone
23. Systemic vasodilator
24. Nitric Oxide generator
25. Reduces gray matter plaque build-up
26. Blocks or retards development of gray matter plaque
27. Reverses arteriosclerosis
28. Prevents arteriosclerosis in most people, while significantly retarding its development in the others
29. Lowers blood pressure in people with higher than healthy blood pressure without lowering blood pressure to unsafe levels
30. Relieves angina pain
31. Increases blood flow
32. Improves blood flow
33. Causes surgical wounds to heal faster
34. Restores blood flow to extremities
35. Reverses several symptoms of type II diabetes
36. Lowers cognition age
37. Increases mental concentration
38. Lowers LDL cholesterol
39. Raises HDL cholesterol
40. Protects against bacterial infection
41. Protects against viral infection
42. Makes skin more elastic
43. Increases the quality of skin cell formation
44. Reduces psoriasis
45. Reduces acne
46. Reduces eczema
47. Substantially decreases the spread of cancer
48. Increases the effectiveness of chemotherapy and other anti-cancer drugs 49. Effective treatment for erectile dysfunction
50. Improves firmness of erection
51. Increases frequency of erections
52. Reduces stimulation required to get an erection
53. Increases sex drive
54. Relieves arthritis pain
55. Relieves joint pain
56. Relieves fibromyalgia pain
57. Rebuilds damaged joints
58. Relieves pain from restless leg syndrome
59. Relieves asthma
60. Relieves hayfever symptoms
61. Reduces bone loss after menopause
62. Increases estrogen in women
63. Reduces PMS symptoms
64. Reduces risk of stroke
65. Reduces risk of heart attack
66. Reduces risk of heart disease
67. Reduces symptoms of mitral valve prolapse
68. Reduces risk of Type II diabetes in overweight people
69. Improves sperm quality
70. Reverses certain types of male infertility
71. Eliminates or reduces intermittent claudicating arteries
72. Improves kidney function in patients taking cyclosporine
73. Increases the time between dialysis treatments
74. Increases magnesium serum concentration in patients with damaged kidneys
75. Effective treatment for migraine headache The present invention is exemplified with respect to a formulation actually made and tested for use in sexual dysfunction. However, this is exemplary only, and the invention can be broadly applied to any of the formulations described herein and in any of the uses described herein. The following experiments are intended to be illustrative only, and not unduly limit the scope of the appended claims.

Experiment 1

Formulations

Three separation formulations containing the ingredients listed below were prepared. Formula 1 has been optimized for both men and women, is non-residual, and is the most potent formula available that is still World Anti-Doping Agency (WADA) compliant. Furthermore, it has been tested for efficacy, as described below Only USP Grade materials (tested per the United States Pharmacopeia monograph procedures) were used, and all inbound materials are tested before use, and kept in quarantine until approved. An FT-NIR Analyzer was used for quantitative and qualitative testing of ingredients to show both purity and reproducibility, especially with respect to naturally sourced ingredients. High Performance Liquid Chromatography, Gas Chromatography, Mass Spectrometry, and Melting Point analysis were also used as needed. In addition to confirming ingredients, microbiological testing was performed, as well as each ingredient screened for steroids, melamine and other unwanted substances or filler that may have been put into the raw material.

The active ingredients shown below are combined as dry powders and blended. The blend is then processed for time release using a coating of magnesium stearate, and including a small amount of powdered silica to prevent caking and absorb moisture.

Finally, gelatin capsules are filled with the pellets, to provide the dosage levels below in 6 daily capsules.

| Formula 1 - daily dosage |
|---|
| 2000 mg L-Arginine |
| 1000 mg L-Citrulline |
| 1000 mg L-Carnitine (as carnitine tartrate) |
| 30 mg Zinc (as zinc sulfate) |
| 400 mg Magnesium (as magnesium citrate) |

Efficacy

FORMULA 1 was tested for efficacy in improving male erectile function and female sexual desire. Using the below-listed clinical tools, FORMULA 1 demonstrated statistically significant improvements in both male and female sexual functioning. For women, FORMULA 1 increased sexual desire, sexual arousal, orgasm satisfaction and lubrication. For men, FORMULA 1 improved erectile functioning and increased sexual desire.

FSFI (Female Sexual Functioning Index)

A 19-item questionnaire called the FSFI was developed as a brief, multidimensional self-report instrument for assessing the key dimensions of sexual function in women. It was developed on a female sample of normal controls and age-matched subjects who met DSM-IV®-TR criteria for female sexual arousal disorder (FSAD) and provides scores on six domains of sexual function (desire, arousal, lubrication, orgasm, satisfaction, and pain) as well as a total score. The FSFI has been validated on clinically diagnosed samples of women with female sexual arousal disorder (FSAD), female orgasmic disorder (FOD), and hypoactive sexual desire disorder (HSDD). See Weigel 2005. Therefore, it is a suitable tool for scoring efficacy data.

A total of 50 women were selected based on being clinically diagnosed with female sexual arousal disorder (FSAD), female orgasmic disorder (FOD), and hypoactive sexual desire disorder (HSDD). The participants were divided into two groups. Group 1: FSFI Full Scale baseline mean=12.967 (Low functioning) Group 2: FSFI Full Scale baseline mean=23.740 (Mid functioning). The women took 6 capsules/day for 90 days for 3 months.

Women were scored at t=0, 30, 60 and 90 days based on the FSFI questionnaire. The data are shown in FIG. 8-14. These figures show statistically significant changes; increased scores indicate improvement in sexual function:

| | |
|---|---|
| FSFI Full Scale Score | +12.05 p < .01 |
| FSFI Desire | +2.10 p < .01 |
| FSFA Arousal | +2.30 p < .01 |
| FSFI Lubrication | +2.28 p = .02 |
| FSFI Orgasm | +2.00 p = .01 |
| FSFI Satisfaction | +1.45 p = .02 |
| FSFI Pain | +2.15 p = .03 |

IIEF (International Index of Erectile Function)

The IIEF is another questionnaire designed to assess for treatment-related changes among patients with erectile dysfunction. The questionnaire contains 15 items that are rated on a 6-point Likert scale, which assess four domains of male sexual dysfunction: erectile function, orgasmic function, sexual desire, and intercourse satisfaction. See Rosen 1997.

200 number of men were selected based on being clinically diagnosed with erectile disorder (ED). The IIEF participants were divided into two groups. Group 1: IIEF Erectile Function baseline mean>14 (ED with mid erectile function) Group 2: IIEF Erectile Function baseline mean<14 (ED with mid erectile function). The men took 6 capsules/day for 90 days for 90 days.

Although the graphs are not shown herein, statistically significant changes (increased scores indicate improvement in sexual function) were observed.

| | |
|---|---|
| IIEF Full Scale Score | +8.75 p < .01 |
| IIEF Erectile Function | +3.49* p = .03 |
| IIEF Sexual Desire | +1.42 p < .01 |
| IIEF Overall Satisfaction | +1.77 p = .02 |

*IIEF participants with low erectile function baseline scores (<14) exhibited a statistically significant improvement of +6.52 p < .01 in the erectile function domain and a statistically significant improvement of +2.41 p < .01 in the sexual desire domain. Both improvements exhibited at the 60 day evaluation point.

PHQ-9 (Patient Health Questionnaire)

The PQ9 is widely used in primary care clinics, outpatient offices, and longitudinal research studies to monitor a patient's symptoms of depression. This questionnaire is comprised of 9 items that correspond with the diagnostic criteria for depression included in the Diagnostic and Statistical Manual of Mental Disorders, 4th Edition (DSM-IV). Each statement is rated on a 4-point, Likert scale.

Figure 15:
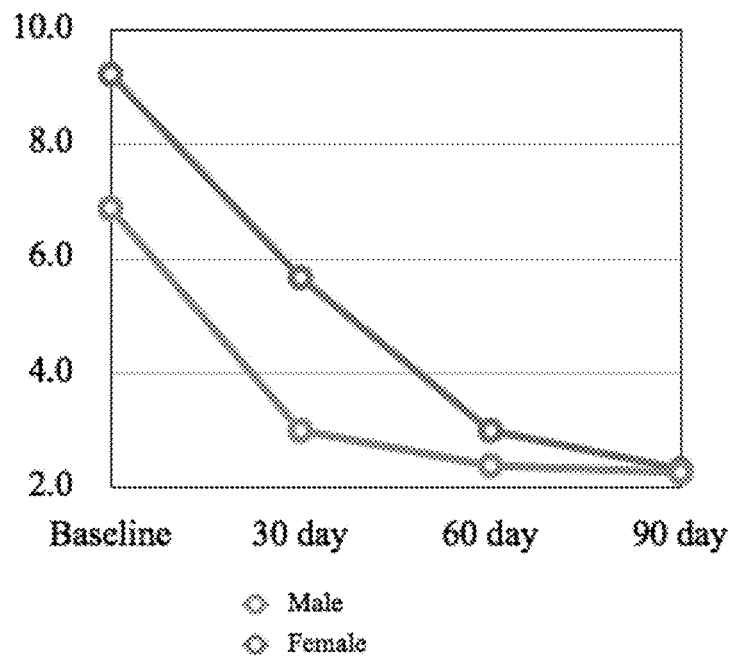
FIG. 15: PHQ9 (men and women)

Each of the patients above (men and women) was also provided with the PQ9 at 30 and 60 days. The PHQ-9 results exhibited statistically significant improvements in depressive symptoms occurred for males after 30 days (p<0.001) and for females after 60 days (p<0.01). These improvements from baseline were maintained at the 60 and 90 day follow-up (p<0.001), respectively (see FIG. 15). Decreased scores indicate reduction in symptoms of depression.

ADAM (Androgen Deficiency in Aging Males)

Figure 16:
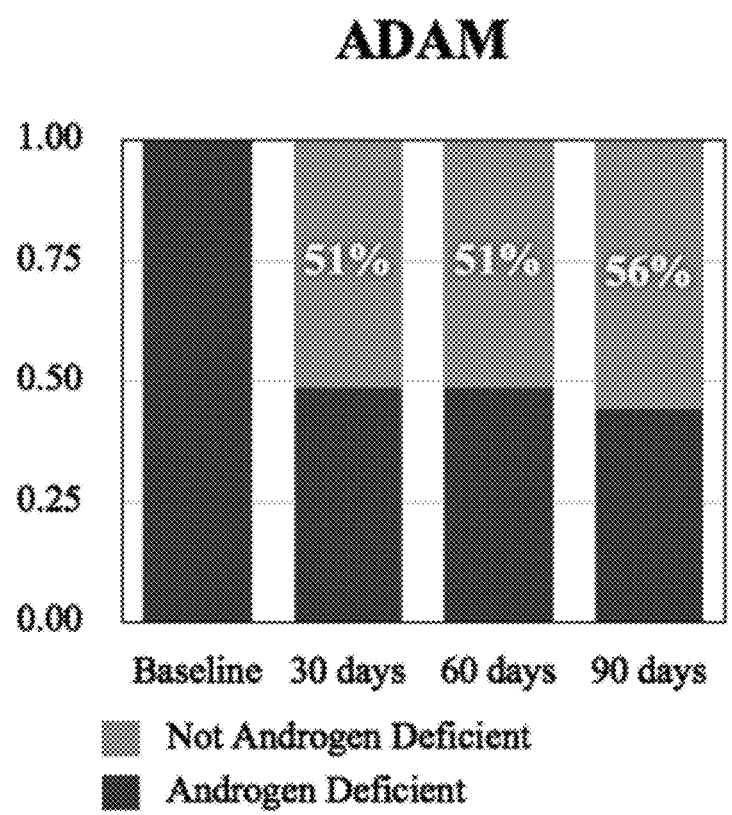
FIG. 16: ADAM ANDROGEN DEFICIENCY
FIGS. 17A-B provides additional formulations

The ADAM is designed to assess for symptoms of low testosterone. The questionnaire contains 10 items. The men were also given the ADAM questionnaire ar 30, 60 and 90 days. The results are shown in FIG. 16. Over half (51.2%) of the men meeting criteria for androgen deficiency at baseline no longer met criteria after 30 days of FORMULA 1 supplementation. The percentage held constant at 60 days. After 90 days of FORMULA 1 supplementation, 55.8% of the men meeting criteria for androgen deficiency at baseline no longer met criteria. The labeled/green areas indicate the percentage of men whose ADAM results indicated androgen deficiency at Baseline who subsequently indicated not likely to be androgen deficient after taking FORMULA 1 for the time period noted on the x-axis.

The following references are incorporated by reference in their entirety for all purposes.

Wiegel M, et al., The female sexual function index (FSFI): cross-validation and development of clinical cutoff scores, J Sex Marital Ther. 31(1):1-20 (2005).

Rosen R. C., et al., The international index of erectile function (IIEF): a multidimensional scale for assessment of erectile dysfunction. Urology 49(6):822-30 (1997).

U.S. Pat. No. 8,802,162. L-citrulline for treating endothelial dysfunction and erectile dysfunction U.S. Pat. No. 6,028,107 Orthomolecular medical use of L-citrulline for vasoprotection, relaxative smooth muscle tone and cell protection U.S. Pat. No. 8,609,735 Rapid-acting, blood-arginine-level-increasable oral preparation comprising citrulline and arginine US20140255528 Compositions and methods for treating, inhibiting the onset, and slowing the progression of erectile dysfunction including naturally occurring age related erectile dysfunction US20040235953 Administering nitric oxide precursor selected from citrulline, arginine to prevent hepatitis, cirrhosis, pulmonary hypertension, necrotizing enterocolitis (NEC), acute respiratory distress syndrome, erectile dysfunction and bone marrow transplant toxicity U.S. Pat. No. 7,645,742 Administering a formulation containing creatine, L-arginine-alpha-ketoglutarate, D-ribose, L-carnitine, L-citrulline, and pyruvate to a mammal performing a physical activity 15-30 minutes before initiation of the physical activity; increases endurance and muscle mass of the person U.S. Pat. No. 5,270,472 Alkanoyl L-carnitine amides with aminoacids and pharmaceutical compositions containing same for promoting regeneration of the nervous tissue, inhibiting neuronal degeneration, enhancing the process of learning and memory and for the treatment of coma.

The invention claimed is:

1. A composition of matter, comprising 1-2 parts L-arginine, 1-2 parts L-citrulline, 1-2 parts L-carnitine, and one or more of 0.02-0.05 parts zinc, 0.3-0.6 parts magnesium, 0.5-1 part *ginseng*, and 0.7-1.2 parts *Epimedium*, formulated as a time release formulation.

2. The composition of claim 1, formulated with magnesium stearate to slow dissolution.

3. The composition of claim 1, having the following active ingredients for a daily dosage:

| |
|---|
| 2000 mg L-Arginine |
| 1000 mg L-Citrulline |
| 1000 mg L-Carnitine |
| 30 mg Zinc |
| 400 mg Magnesium |
| or |
| 2000-4000 mg L-Arginine |
| 1000-2000 mg L-Citrulline |
| 1000-2000 mg L-Carnitine |
| 10-40 mg Zinc |
| 100-400 mg Magnesium |
| or |
| 1000 mg L-Arginine |
| 1000 mg L-Citrulline |
| 1000 mg L-Carnitine |
| 900 mg Panax Ginseng |
| 1000 mg Epimedium |
| 50 mg DHEA |
| or |
| 2000 mg L-Arginine |
| 2000 mg L-Citrulline |
| 2000 mg L-Carnitine |
| 30 mg Zinc |
| 400 mg Magnesium |
| 900 mg *Panax Ginseng* |
| or |
| 1000 mg L-Arginine |
| 1000 mg L-Citrulline |
| 1000 mg L-Carnitine |
| 300-500 mg ginsenosides |
| 50-100 mg icariin |
| 25-50 mg DHEA. |

4. The composition of claim 3, wherein said carnitine is provided as carnitine tartrate, said zinc is provided as zinc sulfate, and said magnesium is provided as magnesium citrate.

5. The composition of matter of claim 1, wherein every ingredient is pharmaceutical grade.

6. The composition of matter of claim 1, wherein said composition is in the form of pellets inside a capsule.

7. The composition of matter of claim 1, wherein said composition is in the form of time-release pellets inside a gelatin capsule.

8. The composition of matter of claim 2, wherein said composition is in the form of time-release pellets inside a gelatin capsule.

9. The composition of matter of claim 3, wherein said composition is in the form of time-release pellets inside a gelatin capsule.

10. A method of making a time release formula of the composition of matter according to claim 1 for treating sexual dysfunction, said method comprising:
   a) blending 1-2 parts L-arginine, 1-2 parts L-citrulline, 1-2 parts L-carnitine, and one or more of 0.02-0.05 parts zinc, 0.3-0.6 parts magnesium, 0.5-1 part *ginseng*, and 0.7-1.2 parts *Epimedium*;
   b) making pellets from the blend of step a);
   c) filling capsules with the pellets of step b).

11. The method of claim 10, further comprising coating said pellets with magnesium stearate.

12. A method of treating female sexual dysfunction, comprising administering the composition according to claim 1 to a female patient having a sexual dysfunction daily for a period of at least 30 days.

13. The method of claim 12, comprising administering the composition for a period of at least 60 days.

14. The method of claim 12, comprising administering the composition for a period of at least 90 days.

15. The method of claim 12, wherein said female sexual dysfunction is female sexual arousal disorder (FSAD), female orgasmic disorder (FOD), or hypoactive sexual desire disorder (HSDD).

\* \* \* \* \*